(12) United States Patent
Hoefle et al.

(10) Patent No.: US 6,982,280 B1
(45) Date of Patent: Jan. 3, 2006

(54) EPOTHILONE DERIVATIVES, A METHOD FOR THE PRODUCTION THEREOF, AND THEIR USE

(76) Inventors: Gerhard Hoefle, Mascheroder Weg 1, D-38124 Braunschweig (DE); Thomas Leibold, Mascheroder Weg 1, D-38124 Braunschweig (DE)

( * ) Notice: Subject to any disclaimer, the term of this patent is extended or adjusted under 35 U.S.C. 154(b) by 0 days.

(21) Appl. No.: 09/674,877

(22) PCT Filed: May 7, 1999

(86) PCT No.: PCT/EP99/03159

§ 371 (c)(1),
(2), (4) Date: Jan. 2, 2001

(87) PCT Pub. No.: WO99/58534

PCT Pub. Date: Nov. 18, 1999

(30) Foreign Application Priority Data

May 8, 1998 (DE) ................ 198 20 599

(51) Int. Cl.
*A61K 31/365* (2006.01)
*C07D 493/02* (2006.01)
(52) U.S. Cl. .............. 514/450; 549/270; 549/213; 549/271
(58) Field of Classification Search ........ 549/270, 549/271, 213; 514/450
See application file for complete search history.

(56) References Cited

U.S. PATENT DOCUMENTS 6,380,394 B1   4/2002   Nicolaou et al.

FOREIGN PATENT DOCUMENTS

| DE | DEX 195 42 986 | 5/1997 |
| WO | WO 93/10121 | 5/1993 |
| WO | WO/97/19086 | 5/1997 |
| WO | WO 98/22461 | 5/1998 |
| WO | WO 99/67252 | 12/1999 |

OTHER PUBLICATIONS

Nicolaou, K.C. et al. : Total synthesis of Oxazole- and cyclopropane-containing Epothilone B analouges by the macrolactonization approach. Chem Eur. J. vol. 3, pp. 1971-19896, 1997.*
U.S. Appl. No. 08/856,533, filed 05/14/97, Nicolaou et al.
Balog et al., 1996, "Total Synthesis of (-)-Epothilone A", Angew. Chem. Int. Ed. Engl. 35:2801-2803.
Gerth et al., 1996, "Epothilons A and B: Antifungal and Cytotoxic Compounds from *Sorangium cellulosum* (Myxobacteria) Production, Physico-chemical and Biological Properties", J. of Antibiotics 49:560-563.
Hofle et al., 1996, "Epothilone A and B—Novel 16-Membered Macrolides with Cytotoxic Activity: Isolation, Crystal Structure, and Conformation in Solution", Angew. Chem. Int. Ed. 35:1567-1569.
Hofle et al., 1999, "N-Oxidation of Epothilone A-C and O-Acyl Rearrangement to C-19 and C-21 Substituted Epothilones", Angew. Chem. Int. Ed. 38:1971-1974.
Nicolaou et al., 1997, "Total Synthesis of Oxazole- and Cyclopropane-Containing Epothilone B Analouges by the Macrolactonization Approach", Chem. Eur. J. 3:1971-1986.
Nicolaou et al., 1998, "Total Synthesis of Epothilone E and Analouges with Modified Side Chain Reactions through the Stille Coupling Reaction", Angew. Chem. Int. Ed. 37:84-87.
Nicolaou et al., 1997, "Designed Epothilones; Combinatorial Synthesis, Tubulin Assembly Properties, and Cytotxic Action against Taxol-Resistant Tumor Cells", Angew. Che. Int. Ed. Engl. 36:2097-2103.
Nicolaou et al., 1997, "Total synthesis of Oxazole- and Cyclopropane-Containing Epothilone A Analogues by the Olefin Metathesis Approach", Chem. Eur. J. 3: 1957-1970.

* cited by examiner

*Primary Examiner*—Charanjit S. Aulakh

(57) ABSTRACT

The present invention relates to epothilon derivatives, processes for their production and their use in the manufacture of medicaments and plant protection agents.

21 Claims, No Drawings

EPOTHILONE DERIVATIVES, A METHOD FOR THE PRODUCTION THEREOF, AND THEIR USE

This application is a 371 of PCT/EP99/03159 filed May 7, 1999, now WO99/58534 Nov. 18, 1999.

The present invention relates generally to epothilon derivatives, to processes for their production and to their use in the manufacture of medicaments and plant protection agents. The invention relates especially to epothilon derivatives of the general formulae 2 to 6 shown below and to their use as medicaments and plant protection agents.

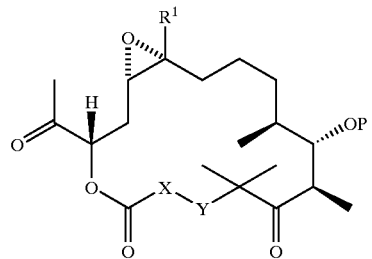

2

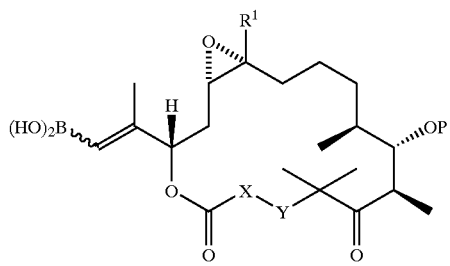

3

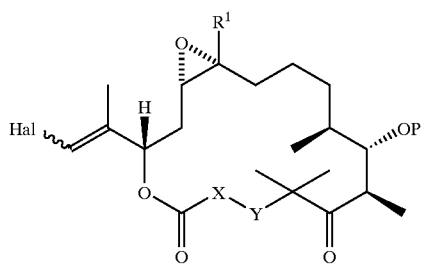

4

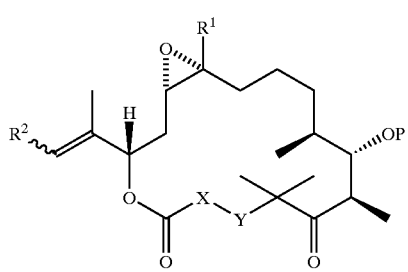

5

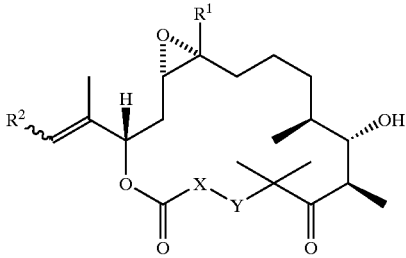

6

In the above formulae:

$R^1$=a H atom or a $C_1$- to $C_8$-alkyl group, preferably a $C_1$- to $C_6$-alkyl group, especially preferably a $C_1$- to $C_4$-alkyl group, especially a methyl, ethyl, propyl or butyl group, $R^2$=a monocyclic aromatic group, such as a 5- or 6-membered aromatic group (such as a phenyl ring) or a vinyl group, each of which may be substituted in the ortho- and/or meta- and/or para-position(s) by one, two, three, four or five, especially one or two, halogen atoms and/or $OR^4$ and/or $NR^5R^6$ groups and/or alkyl and/or alkenyl and/or alkynyl groups, wherein $R^4$, $R^5$ and $R^6$ each independently of the others have the same meanings as $R^1$, but are independent of $R^1$, or $R^2$=a monocyclic 5- or 6-membered heteroaromatic group which may have one or more, especially one or two, O and/or N and/or S atoms in the ring and/or may have $OR^4$ and/or $NR^5R^6$ groups and/or alkyl and/or alkenyl and/or alkynyl groups as substituents, wherein $R^4$, $R^5$ and $R^6$ are as defined above. In the definition of $R^2$ there are especially preferred $C_1$–$C_6$-alkyl or $C_2$–$C_6$-alkenyl and -alkynyl groups, especially $C_1$–$C_4$-alkyl or $C_2$–$C_4$-alkenyl and -alkynyl groups. As alkyl groups there are especially preferred methyl, ethyl, propyl and butyl groups and as heteroaromatic groups 6-membered heteroaromatic groups, Hal=a halogen atom, such as Br or I, X—Y=a group of the formula —CH$_2$CH—OP or —CH=CH—, and P=a protecting group, such as TMS.

The compounds according to the invention may be produced as follows:

Compounds of the formula (2) may be produced by reacting compounds of the formula (1)

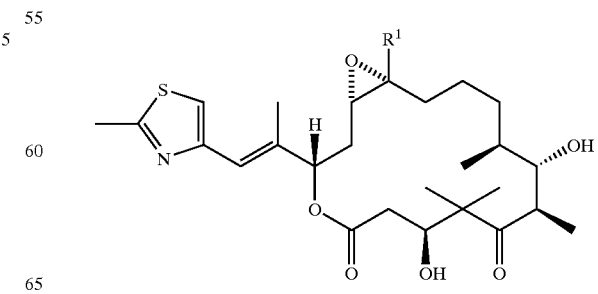

as described in DE 195 42 986, the radicals being as defined above. In that reaction, especially the following conditions (i), (iii) and optionally (after (i)) also (ii) may be used:

(i)
(a) $O_3$ in a solvent, such as $CH_2Cl_2$, and
(b) reductive working-up, for example with $Me_2S$;

(ii)
(a) $(CH_3CO)_2O$, $HCO_2H$, $NEt_3$, DMAP;
(b) DBU; and
(c) MeOH, $NH_3$; and (iii) $Me_3SiCl$, $NEt_3$.

Compounds of the formula (3) are obtainable by reacting a compound of the formula (2) with a compound of the formula $HC[B(OR)_2]_3$, such as tris(ethylenedioxyboryl)methane; R may be an alkyl or alkenyl group as defined above.

In the reaction there is optionally used a strong base, such as a $C_1$–$C_4$-alkyl-Li compound (such as butyllithium) or a di-$C_1$–$C_4$-alkylamine-Li compound (such as a dimethylamine-lithium compound). The reaction is generally carried out at low temperatures, such as, for example, at temperatures of less than −30° C., preferably at temperatures of less than −50° C., especially preferably at temperatures of at least −78° C. Further reaction conditions may be found in D. Schummer, G. Höfle in *Tetrahedron* 1995, 51, 11219.

For example, a compound of the formula (2) is reacted with tris(ethylenedioxyboryl)methane and butyllithium at −78° C. to form a compound of the formula (3).

A compound of the formula (4) may be produced from a compound of the formula (3) by reaction with N-iodo- or N-bromo-succinimide, optionally in a polar solvent, such as acetonitrile. Further reaction conditions may be found in the following literature reference: N. A. Petasis, I. A. Zavialor, *Tetrahedron Lett.* 1996, 37, 567.

For the production of a compound of the formula (5), a compound of the formula (3) may be reacted within the framework of a Suzuki coupling with a compound of the formula $R^2$—Z, wherein $R^2$ has the meanings given above and Z may be a halogen atom or a group of the formula —$OSO_2CF_3$, —CH=CHI, —CH=$CHOSO_2CF_3$. The group $R^2$—Z may especially have the following structures:

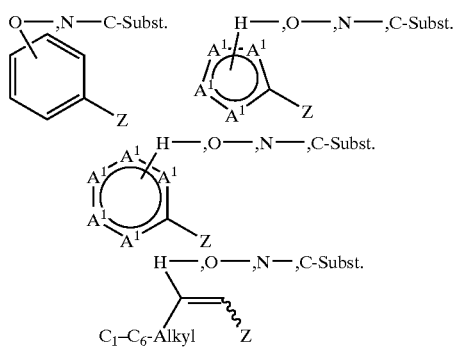

wherein $A^1$ represents O, S, N or C atoms and the substituents O—, N— and C— correspond to the above-described groups $OR^4$, $NR^5R^6$ and alkyl, alkenyl and/or alkynyl groups.

Especially preferred as substituents "C" are $C_1$–$C_6$-alkyl or $C_2$–$C_6$-alkenyl and/or -alkynyl groups, especially $C_1$–$C_4$-alkyl or $C_2$–$C_4$-alkenyl and/or -alkynyl groups. As alkyl groups there are especially preferred methyl, ethyl, propyl and butyl groups.

Alternatively, a compound of the formula (5) may be produced by reacting a compound of the formula (4) by means of a Stille coupling with $R^2$—$SnR^3_3$, wherein $R^2$ is as defined above and $R^3$ is a $C_1$- to $C_6$-alkyl group, preferably a $C_1$- to $C_4$-alkyl group and especially preferably a methyl, ethyl, propyl or butyl group. In addition, the compound $R^2$—$SnR^3_3$ may have one of the following structures:

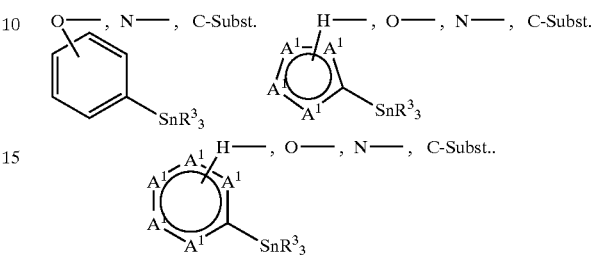

wherein the radicals and substituents are as defined above.

Furthermore, according to the invention, a compound of the formula (6) may be produced by removing the protecting group from the compound of the formula (5), for example with a weak acid, such as citric acid, or compounds such as TBAF, pyridine×HF. Optionally an alcohol, such as methanol, may be used as solvent, the temperature preferably being adjusted to values of, for example, from 40 to 60° C., preferably about 50° C.

In summary, the compound of the formula (6) may be produced by the above-described steps (epothilon A or B→(2)→(3)→(4)→(5)→(6) or epothilon A or B →(2)→(3) →(5)→(6)).

According to the invention there are also disclosed medicaments that contain at least one of the compounds (2), (3), (4), (5) or (6) and optionally customary carriers, diluents and adjuvants.

Such compounds may especially be used also as cytostatic agents and for plant protection in agriculture and/or forestry and/or in horticulture, the compounds optionally being used together with one or more customary carriers, adjuvants and/or diluents.

EXAMPLES

Synthesis of the Ketone Derivatives 2
For a detailed description see DE 195 42 986 A1.

Synthesis of the Alkenylboronic Acid Derivatives 3

(see also D. Schummer, G. Höfle, *Tetrahedron* 1995, 51, 11219)

Typical Example ($R^1$=H, X—Y=$CH_2CHOTMS$):

A solution of tris(ethylenedioxyboryl)methane (0.30 g, 1.5 mmol) in $CH_2Cl_2$/THF (1:1; 4 ml) was prepared and cooled under inert gas to −78° C. At that temperature, butyllithium (1.6M solution in hexane; 0.73 ml, 1.2 mmol) was added dropwise wise in the course of 10 minutes. After 2 hours, ketone 2 (81 mg, 0.15 mmol) in $CH_2Cl_2$/THF (1:1, 2 ml) was added, heated to room temperature and stirred for 17 hours. After the addition of MeOH (2 ml), the clear reaction solution was purified by means of preparative HPLC (Lichroprep RP-18, $CH_3CN/H_2O$ 75:25). 57 mg (65%) of alkenylboronic acid 3 were obtained in the form of an E/Z-isomeric mixture (6:4).

Selected typical data: LC-MS (ESI-MS): 585 ($M^+$+H); $^1$H-NMR: (300 MHz, $CD_3OD$): E-isomer: 1.91 (S, 3H), 5.16

(d, 1H, 10 Hz), 5.49 (s, 1H), Z-isomer; 1.85 (d, 3H, 1.1 Hz), 4.93 (s, 1H), 5.26 (d, 1H, 9.6 Hz).

Synthesis of the Iodovinyl Derivatives 4

(see also N. A. Petasis, I. A. Zavialor, *Tetrahedron Lett.* 1996, 37, 567)

Typical Example ($R^1$=H, X—Y=$CH_2$CHOTMS):

At room temperature, N-iodosuccinimide (6.0 mg, 27 µmol) was added under inert gas and with the exclusion of light to a solution of alkenylboronic acid 3 (12 mg, 21 µmol; E/Z 9:1) in $CH_3CN$ (150 µl) and stirred for 3 hours. After concentration, the residue was purified by means of preparative thin-layer chromatography ($SiO_2$, $CH_2Cl_2$/MeOH 95:5). 9 mg (66%) of the iodovinyl derivative 4 were isolated in the form of an E/Z-isomeric mixture (9:1).

Selected typical data: LC-MS (ESI-MS): 667 ($M^+$+H); $^1$H-NMR: (300 MHz, $CDCl_3$); E-isomer: 1.82 (d, 3H, 1.1 Hz), 5.36 (d, 1H, 11 Hz), 6.43 (s, 1H), Z-isomer: 1.84 (d, 3H, 1.1 Hz), 5.54 (d, 1H, 10.5 Hz), 6.09 (s, 1H).

Suzuki Coupling of the Alkenylboronic Acid 3

(see also A. Suzuki, *Acc. Chem. Res.* 1982, 15, 178; A. Torrado, S. Lopez, R. Alvarez, A. R. De Lera *Synthesis*, 1995, 285)

Typical Example ($R^1$=H, X—Y=$CH_2$CHOTMS, $R^2$=Ph):

A solution of alkenylboronic acid 3 (12 mg, 21 µmol; E/Z 2:8) and thallium ethanolate (2M solution in EtOH; 12 µl, 24 µmol) in THF (150 µl) was stirred at room temperature for 15 minutes, then a solution of phenyl iodide (4.0 µl, 6.0 mg, 29 µmol) and tetrakis(triphenylphosphino)-palladium (7.1 mg, 6.2 µmol) in THF (150 µl) was added dropwise in 30 minutes and again stirred for 30 minutes. After purification by means of preparative thin-layer chromatography ($SiO_2$, $CH_2Cl_2$/$Et_2O$ 95:5) the phenyl-analogous epothilon 5 (10 mg, 79%, E/Z 2:8) was obtained in the form of a colourless solid.

Selected typical data: LC-MS (ESI-MS): 617 ($M^+$+H); $^1$H-NMR: (300 MHz, $CDCl_3$): E-isomer: 1.87 (d, 3H, 1.4 Hz), 5.35 (d, 1H, 10.7 Hz), 6.54 (s, 1H), Z-isomer: 1.80 (d, 3H, 1.5 Hz), 5.61 (d, 1H, 10.2 Hz), 6.41 (s, 1H).

Stille Coupling of the Iodovinyl Derivatives 4

(see also K. C. Nicolaou, Y. He, F. Roschangar, N. P. King, D. Vourloumis, T. Li *Angew. Chem.* 1998, 110, (1/2), 89).

What is claimed is:

1. A compound of the formula:

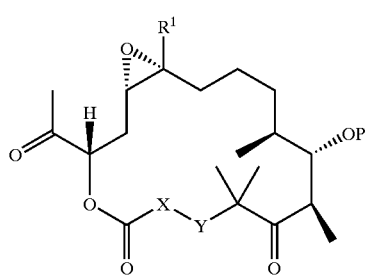

wherein $R^1$ is a H atom or a $C_1$- to $C_8$-alkyl group,

X—Y is a group of the formula —$CH_2$CH(OP)— or —CH=CH—, and

P is a protecting group.

2. A compound of the formula:

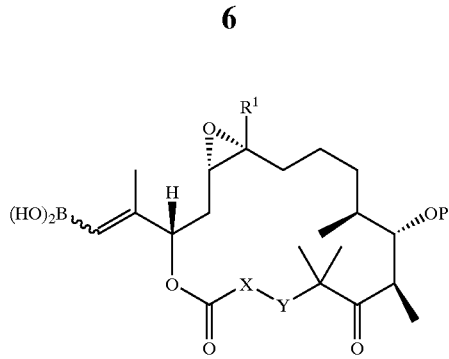

wherein the radicals are as defined in claim 1.

3. A compound of formula:

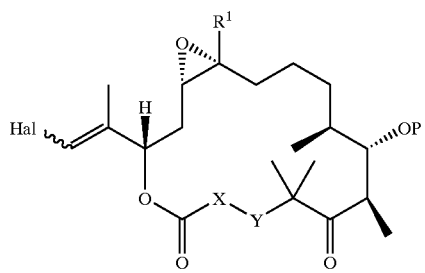

wherein the residues $R^1$, X—Y and P are defined as in claim 1, and Hal is a halogen.

4. A compound of the formula:

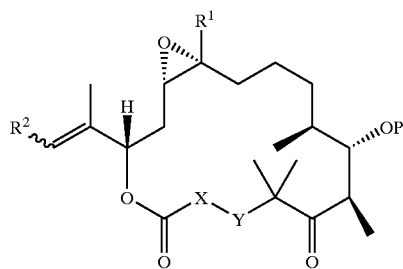

wherein the residue $R^1$ is a hydrogen atom or a $C_{1-8}$-alkyl group, and P is a protective group and X—Y is a group of formula —$CH_2$CH(OP)— or CH=CH, and $R^2$ is a monocyclic aromatic which can be substituted by a halogen atoms and/or $OR^4$- and/or $NR^5R^6$- and/or alkyl, alkenyl and/or alkynyl groups in ortho- and/or meta- and/or para-position, or a monocyclic 5- or 6-membered hetero aromatic, which can be optionally substituted with one or several O- and/or N- and/or S-atoms in the ring and/or which can be optionally substituted with $OR^4$- and/or $NR^5R^6$- and/or alkyl, alkenyl and/or alkynyl groups as substituents, wherein the residues $R^4$, $R^5$ and $R^6$ are each independently a hydrogen atom or a $C_{1-8}$-alkyl group, wherein (i) XY is excluded as group of formula —CH=CH— if $R^1$ is a hydrogen atom or a $C_{1-4}$-alkyl group and $R^2$ is a monocyclic hetero aromatic having a N atom or a N and a S atom in its ring and a $C_1$-alkyl substituent and (ii) XY is excluded as group of formula —$CH_2$CH(OP)— if $R^1$ is a hydrogen atom or a $C_{1-4}$-alkyl group and $R^2$ is a monocyclic hetero aromatic having a N atom or a N and a S atom in its ring and a $C_1$-alkyl substituent.

5. A compound of the formula:

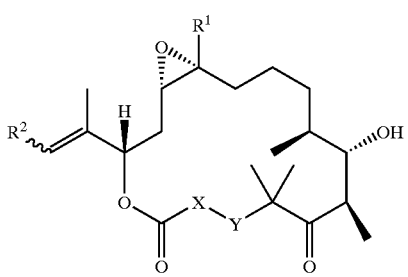

wherein the residues are as defined in claim 4 and, if X—Y means a group of formula —CH$_2$CH—OP, the protective group P has been removed, wherein
  (i) XY is excluded as group of formula —CH═CH— if R$^1$ is a hydrogen atom or a C$_{1-4}$-alkyl group and R$^2$ is a monocyclic hetero aromatic having a N atom and a S atom in its ring and a C$_1$-alkyl substituent and
  (ii) XY is excluded as group of formula —CH$_2$CH(OP)— if R$^1$ is a hydrogen atom or a C$_{1-4}$-alkyl group and R$^2$ is a monocyclic hetero aromatic having a N atom or a N atom and a S atom or a N atom and a O atom in its ring and a C$_1$-alkyl substituent.

6. A compound of formula:

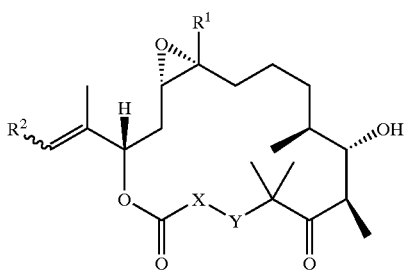

wherein the residues are defined as in claim 4 and, if X—Y means a group of formula —CH$_2$CH(OP)—, the protective group P has been removed, wherein
  (i) XY is excluded as group of formula —CH═CH— if R$^1$ is a hydrogen atom or a C$_{1-4}$-alkyl group and R$^2$ is a monocyclic hetero aromatic having a N atom and/or a S atom in its ring and a C$_1$-alkyl substituent and
  (ii) XY is excluded as group of formula —CH$_2$CH(OP)— if R$^1$ is a hydrogen atom or a C$_{1-4}$-alkyl group and R$^2$ is a monocyclic hetero aromatic having a N atom or a N atom and a S atom or a N atom and an O atom in its ring and a C$_1$-alkyl substituent.

7. A compound as in claims 1, 2, 3, 4, 5 or 6 wherein R$^1$, R$^4$, R$^5$ and R$^6$ are a hydrogen atom or a C$_{1-6}$-alkyl group.

8. A compound as in claims 4, 5, 7 or 6 wherein the substituents of the monocyclic aromatic and/or hetero aromatic are C$_{1-6}$-alkyl, C$_{2-6}$-alkenyl, C$_{2-6}$-alkynyl, fluorine, chlorine, bromine or iodine.

9. A compound as in claims 4, 5, 7, 8 or 6 wherein the monocyclic aromatic and/or monocyclic hetero aromatic is optionally substituted with 1, 2 or 3 substituents and the hetero aromatic is optionally substituted with 1, 2 or more hetero atoms in the ring.

10. Process for the preparation of a compound of the formula:

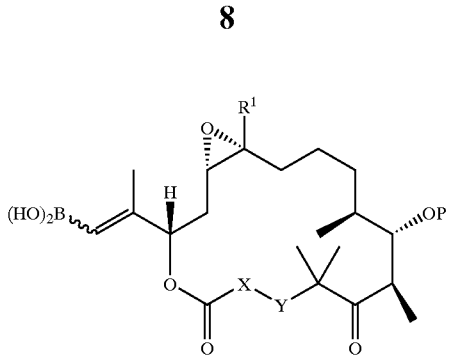

wherein
R$^1$ is a H atom or a C$_1$- to C$_8$-alkyl group,
X—Y is a group of the formula —CH$_2$CH(OP)— or —CH═CH—, and
P is a protecting group,
comprising reacting a compound of the formula:

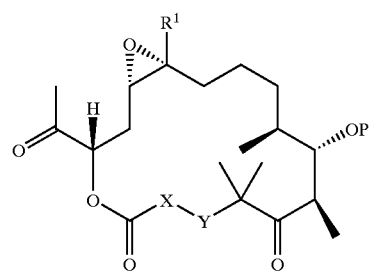

wherein
R$^1$ is a H atom or a C$_1$- to C$_8$-alkyl group
X—Y is a group of the formula —CH$_2$CH(OP)— or —CH═CH—, and
P is a protecting group,
with a compound of the formula HC[B(OR)$_2$]$_3$, wherein R is a H atom or a C$_1$- to C$_8$-alkyl group.

11. Process for the preparation of a compound of the formula:

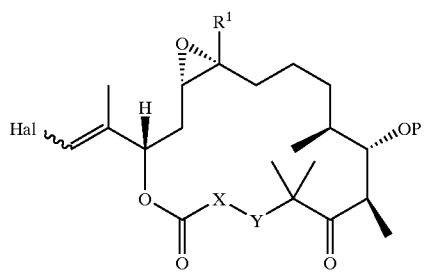

wherein
R$^1$ is a H atom or a C$_1$- to C$_8$-alkyl group,
X—Y is a group of the formula —CH$_2$CH(OP)— or —CH═CH—,
P is a protecting group,
and Hal is a halogen,
comprising reacting a compound of the formula:

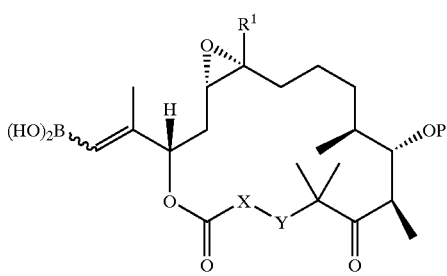

wherein
R¹ is a H atom or a $C_1$- to $C_8$-alkyl group,
X—Y is a group of the formula —$CH_2CH(OP)$— or —CH=CH—, and
P is a protecting group,
with N-iodo or N-bromo-succinimide.

12. Process for the preparation of a compound of formula:

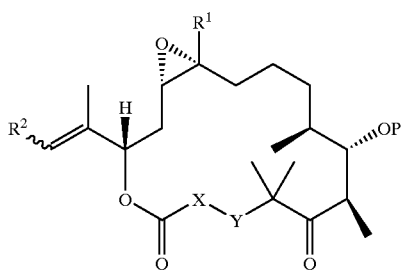

wherein a compound according to claim 2 is reacted by a Suzuki coupling with a compound of formula $R^2$—Z, wherein $R^2$ is a monocyclic aromatic which can be substituted by halogen atoms and/or $OR^4$- and/or $NR^5R^6$- and/or alkyl, alkenyl and/or alkynyl groups in ortho and/or meta- and/or para-position, or a monocyclic 5- or 6-membered hetero aromatic, which can be optionally substituted with one or several O- and/or N- and/or S-atoms in the ring and/or which can be optionally substituted with $OR^4$- and/or $NR^5R^6$- and/or alkyl, alkenyl and/or alkynyl groups as substituents and Z can be a halogen atom or a group of formula —$OSO_2CF_3$, —CH=CHI, —CH=$CHOSO_2CF_3$.

13. Process for the preparation of a compound of formula:

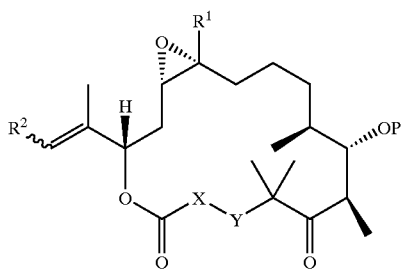

wherein a compound according to claim 3 is reacted by a silent coupling (stille Kupplung) with $R_2$—$SNR^3{}_3$, wherein $R^2$ is a monocyclic aromatic which can be substituted by halogen atoms and/or $OR^4$- and/or $NR^5R^6$- and/or alkyl, alkenyl and/or alkynyl groups in ortho- and/or meta- and/or para-position, or a monocyclic 5- or 6-membered hetero aromatic, which can be optionally substituted with one or several O- and/or N- and/or S-atoms in the ring and/or which can be optionally substituted with $OR^4$- and/or $NR^5R^6$- and/or alkyl, alkenyl and/or alkynyl groups as substituents and $R^3$ is a $C_{1-6}$-alkyl group.

14. Process for the preparation of a compound of formula:

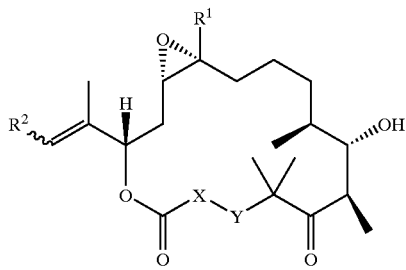

wherein the protective group is removed from a compound according to claim 4.

15. Process for the preparation of a compound of formula:

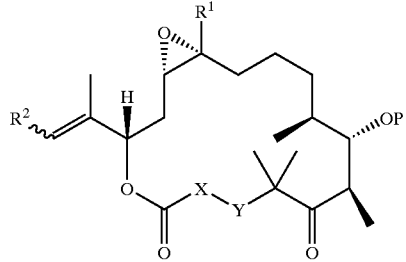

wherein it comprises the process steps as disclosed in claims 10, 11, 12, 13 or 14.

16. A pharmaceutical composition comprising at least one of the compounds described in claims 1, 2, 3, 4, 5, 7, 8, 9 or 6 and optionally carriers, diluents and/or auxiliary agents.

17. The pharmaceutical composition according to claim 16, wherein said compound is cytostaticum.

18. A method of protecting plants in agriculture and/or forest culture and/or horticulture, comprising administering a therapeutically effective amount of at least one compound described in claim 1 and optionally carriers, diluents and/or auxiliary agents.

19. A compound according to claim 6, wherein the substituents of the monocyclic aromatic and/or hetero aromatic are a $C_{1-6}$-alkyl, $C_{2-6}$-alkenyl or $C_{2-6}$-alkynyl group or a halogen atom.

20. A compound according to claim 6, wherein the monocyclic aromatic and/or monocyclic hetero aromatic is optionally substituted with 1, 2 or 3 substituents and the hetero aromatic is optionally substituted with 1, 2 or more hetero atoms in the ring.

21. A compound according to claim 19, wherein the substituents of the monocyclic aromatic and/or hetero aromatic are $C_{1-4}$-alkyl, $C_{2-4}$-alkenyl or $C_{2-4}$-alkynyl groups.

* * * * *

UNITED STATES PATENT AND TRADEMARK OFFICE
CERTIFICATE OF CORRECTION

PATENT NO. : 6,982,280 B1  Page 1 of 1
APPLICATION NO. : 09/674877
DATED : January 3, 2006
INVENTOR(S) : Hoefle et al.

It is certified that error appears in the above-identified patent and that said Letters Patent is hereby corrected as shown below:

Column 6,
Line 48, "and P is a protective group" should read -- and P is a protecting group --.

Column 7,
Lines 16-17 and 43-44, "the protective group P" should read -- the protecting group P --.

Column 9,
Line 63, "silent coupling (stille Kupplung) with $R_2$-SNR$^3{}_3$," should read
-- silent coupling (Stille Kupplung) with $R^2$-Sn($R^3$)$_3$ --.

Signed and Sealed this

Fourth Day of July, 2006

JON W. DUDAS
*Director of the United States Patent and Trademark Office*